(12) United States Patent
Tian et al.

(10) Patent No.: US 11,554,115 B2
(45) Date of Patent: Jan. 17, 2023

(54) QUINOLINE DERIVATIVE FOR TREATMENT OF TRIPLE-NEGATIVE BREAST CANCER

(71) Applicant: CHIA TAI TIANQING PHARMACEUTICAL GROUP CO., LTD., Jiangsu (CN)

(72) Inventors: Xin Tian, Jiangsu (CN); Peng Lv, Jiangsu (CN); Ling Yang, Jiangsu (CN); Xiangjian Wang, Jiangsu (CN); Xiquan Zhang, Jiangsu (CN); Shanchun Wang, Jiangsu (CN); Xunqiang Wang, Jiangsu (CN); Hai Jiang, Jiangsu (CN)

(73) Assignee: CHIA TAI TIANQING PHARMACEUTICAL GROUP CO., LTD., Jiangsu (CN)

( * ) Notice: Subject to any disclaimer, the term of this patent is extended or adjusted under 35 U.S.C. 154(b) by 128 days.

(21) Appl. No.: 16/980,786

(22) PCT Filed: Mar. 13, 2019

(86) PCT No.: PCT/CN2019/077946
§ 371 (c)(1),
(2) Date: Sep. 14, 2020

(87) PCT Pub. No.: WO2019/174590
PCT Pub. Date: Sep. 19, 2019

(65) Prior Publication Data
US 2020/0405709 A1    Dec. 31, 2020

(30) Foreign Application Priority Data
Mar. 14, 2018    (CN) .......................... 201810206831.2

(51) Int. Cl.
*A61K 31/4709*    (2006.01)
*A61P 35/00*    (2006.01)
*A61K 33/243*    (2019.01)
*A61K 9/00*    (2006.01)
*A61K 31/337*    (2006.01)
*A61K 31/675*    (2006.01)
*A61K 31/704*    (2006.01)
*A61K 31/7068*    (2006.01)

(52) U.S. Cl.
CPC ........ *A61K 31/4709* (2013.01); *A61K 9/0053* (2013.01); *A61K 31/337* (2013.01); *A61K 31/675* (2013.01); *A61K 31/704* (2013.01); *A61K 31/7068* (2013.01); *A61K 33/243* (2019.01); *A61P 35/00* (2018.01)

(58) Field of Classification Search
None
See application file for complete search history.

(56) References Cited

U.S. PATENT DOCUMENTS

| 8,247,423 B2* | 8/2012 | Estok | A61K 31/352 |
| | | | 514/183 |
| 10,251,875 B2* | 4/2019 | Puri | A61P 27/10 |
| 2008/0227811 A1* | 9/2008 | Chen | C07D 239/88 |
| | | | 546/160 |
| 2021/0255168 A1* | 8/2021 | Abu Khabar | A61K 31/519 |

FOREIGN PATENT DOCUMENTS

| CN | 102344438 A | 2/2012 |
| CN | 105311030 A | 2/2016 |
| WO | WO-2008112407 A1 | 9/2008 |

OTHER PUBLICATIONS

International Search Report and Written Opinion for International Application No. PCT/CN2019/077946, State Intellectual Property Office of the P.R. China, China, dated Jun. 19, 2019, 15 pages (with English Translation).

* cited by examiner

*Primary Examiner* — Melissa S Mercier
(74) *Attorney, Agent, or Firm* — Ping Wang; Rimon Law

(57) ABSTRACT

The present invention provides a quinoline derivative for treating triple-negative breast cancer and use thereof in preparing a pharmaceutical composition for treating a tumor. Specifically, the present invention relates to use of quinoline derivative 1-[[[4-(4-fluoro-2-methyl-1H-indol-5-yl)oxy-6-methoxyquinoline-7-yl]oxy]methyl]cyclopropylamine in the treatment of triple-negative breast cancer,

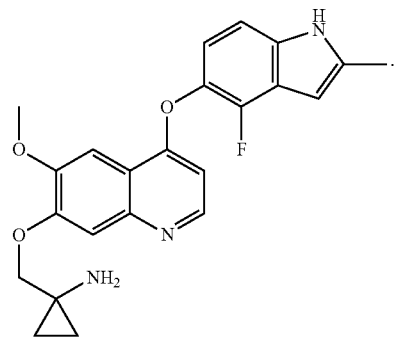

20 Claims, No Drawings

QUINOLINE DERIVATIVE FOR TREATMENT OF TRIPLE-NEGATIVE BREAST CANCER

TECHNICAL FIELD

The present invention relates to the field of pharmaceuticals, and particularly to use of a quinoline derivative in preparation of a pharmaceutical composition for treating tumors. More particularly, the present invention relates to use of the quinoline derivative in treatment of triple-negative breast cancer.

BACKGROUND

Triple-negative breast cancer (TNBC) is a breast cancer that is negative for expression of estrogen receptors (ER), progesterone receptors (PR), and human epidermal growth factor receptor-2 (HER2). In 1.70 million newly diagnosed breast cancer cases worldwide per year, about 15-20% are TNBC. TNBC has unique pathological and clinical features and is characterized by aggressive phenotypes, high metastasis rates, and poorer prognosis compared with other breast cancers. The 5-year survival rate is 70% for patients with TNBC, and is approximately 80% for patients with other breast cancers.

TNBC can be divided into 7 subtypes (6 definable subtypes and 1 unstable subtype): basal-like (BL), mesenchymal (M), mesenchymal stem-like (MSL), luminal androgen receptor (LAR), immunomodulatory (IM), and unstable (UNS) subtypes. BL is further divided into BL1 and BL2.

TNBC is refractory to targeted hormone therapy, such as tamoxifen and aromatase inhibitors, and HER2-targeted drugs, such as herceptin. Chemotherapy is still the standard treatment for TNBC, although it is generally accompanied by limited efficacy and low survival rate. Limited treatment options suggest that there is an urgent need for developing effective therapies for TNBC.

SUMMARY

In one aspect, the present invention provides a method of treating triple-negative breast cancer, comprising administering to a patient in need thereof a therapeutically effective amount of compound I or a pharmaceutically acceptable salt thereof.

In another aspect, the present invention provides a use of compound I or a pharmaceutically acceptable salt thereof in treating triple-negative breast cancer, or in preparing a medicament for treating triple-negative breast cancer.

In yet another aspect, the present invention provides a pharmaceutical composition for treating triple-negative breast cancer, comprising compound I or a pharmaceutically acceptable salt thereof, and at least one pharmaceutically acceptable carrier.

In yet another aspect, the present invention provides a kit for treating triple-negative breast cancer, comprising (a) at least one unit dose of a pharmaceutical composition comprising compound I or a pharmaceutically acceptable salt thereof and (b) a package insert for treating triple-negative breast cancer.

DESCRIPTION OF THE INVENTION

In one aspect, the present invention provides a method of treating triple-negative breast cancer, comprising administering to a patient in need thereof a therapeutically effective amount of compound I or a pharmaceutically acceptable salt thereof.

In some embodiments, the triple-negative breast cancer is an advanced or metastatic triple-negative breast cancer.

In some embodiments, the triple-negative breast cancer is refractory to prior treatment.

In some embodiments, the triple-negative breast cancer is refractory to radiotherapy and/or chemotherapy.

In some embodiments, the triple-negative breast cancer has progressed or relapsed after prior treatment with an anthracycline and/or a taxane. In some embodiments, the triple-negative breast cancer has progressed or relapsed after prior treatment with paclitaxel.

In some embodiments, the triple-negative breast cancer has progressed or relapsed after prior treatment with an antimetabolite. In some embodiments, the triple-negative breast cancer has progressed or relapsed after prior treatment with gemcitabine and/or capecitabine.

In some embodiments, the triple-negative breast cancer has progressed or relapsed after prior treatment with a platinum-based therapy. In some embodiments, the triple-negative breast cancer has progressed or relapsed after prior treatment with cisplatin.

The chemical name of the compound of formula I is 1-[[[4-(4-fluoro-2-methyl-1H-indol-5-yl)oxy-6-methoxy-quinolin-7-yl]oxy]methyl]cyclopropyl amine, which has the following structural formula:

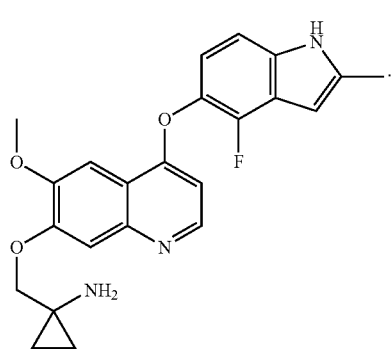 [SMILES: COc1cc2c(Oc3ccc4[nH]c(C)cc4c3F)ccnc2cc1OCC1(N)CC1]

The compound of formula I can be administered in its free base form, or in the form of a salt, a hydrate, or a prodrug that may convert in vivo into a free base form. For example, the pharmaceutically acceptable salt of the compound of formula I can be generated from various organic and inorganic acids according to methods well known in the art, within the scope of the present invention.

In some embodiments, the compound of formula I is administered in a form of hydrochloride. In some embodiments, the compound of formula I is administered in a form of monohydrochloride. In some embodiments, the compound of formula I is administered in a form of dihydrochloride. In some embodiments, the compound of formula I is administered in a crystalline form of hydrochloride. In some embodiments, the compound of formula I is administered in a crystalline form of dihydrochloride. In some embodiments, the compound of formula I is administered in a form of maleate.

The compound of formula I and a pharmaceutically acceptable salt thereof can be administered via multiple routes including, but not limited to, oral, parenteral, intraperitoneal, intravenous, intra-arterial, transdermal, sublingual, intramuscular, rectal, transbuccal, intranasal, inhalational, vaginal, intraocular, topical, subcutaneous, intralipid, intra-articular, intraperitoneal and intrathecal administrations. In a specific embodiment, via oral administration.

The amount of the compound of formula I or a pharmaceutically acceptable salt thereof administered can be determined according to the severity of the disease, the response of the disease, any treatment-related toxicity, and the age and health of a patient. In some embodiments, the daily dose of the compound of formula I or a pharmaceutically acceptable salt thereof is 3 mg to 30 mg. In some embodiments, the daily dose of the compound of formula I or a pharmaceutically acceptable salt thereof is 5 mg to 20 mg. In some embodiments, the daily dose of the compound of formula I or a pharmaceutically acceptable salt thereof is 8 mg to 16 mg. In some embodiments, the daily dose of the compound of formula I or a pharmaceutically acceptable salt thereof is 8 mg to 14 mg. In a specific embodiment, the daily dose of the compound of formula I or a pharmaceutically acceptable salt thereof is 8 mg. In a specific embodiment, the daily dose of the compound of formula I or a pharmaceutically acceptable salt thereof is 10 mg. In a specific embodiment, the daily dose of the compound of formula I or a pharmaceutically acceptable salt thereof is 12 mg.

The compound of formula I or a pharmaceutically acceptable salt thereof can be administered once or multiple times daily. In some embodiments, the compound of formula I or the pharmaceutically acceptable salt thereof is administered once daily. In one embodiment, the compound of formula I or the pharmaceutically acceptable salt thereof is administered once daily in a form of a solid oral preparation.

The regimen can be determined comprehensively depending on the activity and toxicity of the medicament, tolerance of the patient, etc. Preferably, the compound I or a pharmaceutically acceptable salt thereof is administered in an intermittent regimen. The intermittent regimen includes treatment periods and rest periods. In the treatment period, the compound of formula I or the pharmaceutically acceptable salt thereof can be administered once or multiple times daily. For example, the compound of formula I or the pharmaceutically acceptable salt thereof is administered daily in the treatment period, and then the treatment is interrupted during the rest period, followed by the treatment period and then the rest period, over and over again. The ratio of the treatment period to the rest period in days is 2:0.5-2:5, preferably 2:0.5-2:3, more preferably 2:0.5-2:2, and most preferably 2:0.5-2:1.

In some embodiments, the treatment is administered for 2 weeks and interrupted for 2 weeks. In some embodiments, the treatment is administered once daily for 14 days, and interrupted for 14 days; and then administered once daily for 14 days, and interrupted for 14 days, etc. Such intermittent regimen in 2-week treatment/2-week rest cycle can be repeated multiple times.

In some embodiments, the treatment is administered for 2 weeks and interrupted for 1 week. In some embodiments, the treatment is administered once daily for 14 days, and interrupted for 7 days; and then administered once daily for 14 days, and interrupted for 7 days, etc. Such intermittent regimen in 2-week treatment/1-week rest cycle can be repeated multiple times.

In some embodiments, the treatment is administered for 5 days and interrupted for 2 days. In some embodiments, the treatment is administered once daily for 5 days, and interrupted for 2 days; and then administered once daily for 5 days, and interrupted for 2 days, etc. Such intermittent regimen in 5-day treatment/2-day rest cycle can be repeated multiple times.

In certain specific embodiments, the treatment is administered once daily at a dose of 12 mg for 2 weeks, and interrupted for 1 week.

In certain specific embodiments, the treatment is administered once daily at a dose of 10 mg for 2 weeks, and interrupted for 1 week.

In certain specific embodiments, the treatment is administered once daily at a dose of 8 mg for 2 weeks, and interrupted for 1 week.

In another aspect, the present invention further provides use of the compound of formula I or a pharmaceutically acceptable salt thereof in treating triple-negative breast cancer, or in the preparing of a medicament for treating triple-negative breast cancer.

In some embodiments, the triple-negative breast cancer is an advanced or metastatic triple-negative breast cancer.

In some embodiments, the triple-negative breast cancer is refractory to prior treatment.

In some embodiments, the triple-negative breast cancer is refractory to radiotherapy or chemotherapy.

In some embodiments, the triple-negative breast cancer has progressed or relapsed after prior treatment with an anthracycline and/or a taxane. In some embodiments, the triple-negative breast cancer has progressed or relapsed after prior treatment with paclitaxel.

In some embodiments, the triple-negative breast cancer has progressed or relapsed after prior treatment with an antimetabolite. In some embodiments, the triple-negative breast cancer has progressed or relapsed after prior treatment with gemcitabine and/or capecitabine.

In some embodiments, the triple-negative breast cancer has progressed or relapsed after prior treatment with a platinum-based therapy. In some embodiments, the triple-negative breast cancer has progressed or relapsed after prior treatment with cisplatin.

The compound of formula I can be administered in its free base form, or in the form of a salt, a hydrate, or a prodrug that may convert in vivo into the free base form. For example, the pharmaceutically acceptable salt of the compound of formula I can be generated from various organic and inorganic acids according to methods well known in the art, within the scope of the present invention.

In some embodiments, the compound of formula I is administered in a form of hydrochloride. In some embodiments, the compound of formula I is administered in a form of monohydrochloride. In some embodiments, the compound of formula I is administered in a form of dihydrochloride. In some embodiments, the compound of formula I is administered in a crystalline form of hydrochloride. In some embodiments, the compound of formula I is administered in a crystalline form of dihydrochloride. In some embodiments, the compound of formula I is administered in a form of maleate.

The compound of formula I and the pharmaceutically acceptable salt thereof can be administered via multiple routes including, but not limited to, oral, parenteral, intraperitoneal, intravenous, intra-arterial, transdermal, sublingual, intramuscular, rectal, transbuccal, intranasal, inhalational, vaginal, intraocular, topical, subcutaneous, intralipid, intra-articular, intraperitoneal and intrathecal administrations. In a specific embodiment, via oral administration.

The amount of the compound of formula I or a pharmaceutically acceptable salt thereof administered can be determined according to the severity of the disease, the response of the disease, any treatment-related toxicity, and the age and health of a patient. In some embodiments, the daily dose of the compound of formula I or the pharmaceutically acceptable salt thereof is 3 mg to 30 mg. In some embodiments, the daily dose of the compound of formula I or the pharmaceutically acceptable salt thereof is 5 mg to 20 mg. In some embodiments, the daily dose of the compound of formula I or the pharmaceutically acceptable salt thereof is 8 mg to 16 mg. In some embodiments, the daily dose of the compound of formula I or the pharmaceutically acceptable salt thereof is 8 mg to 14 mg. In a specific embodiment, the daily dose of the compound of formula I or the pharmaceutically acceptable salt thereof is 8 mg. In a specific embodiment, the daily dose of the compound of formula I or the pharmaceutically acceptable salt thereof is 10 mg. In a specific embodiment, the daily dose of the compound of formula I or the pharmaceutically acceptable salt thereof is 12 mg.

The compound of formula I or a pharmaceutically acceptable salt thereof can be administered once or multiple times daily. In some embodiments, the compound of formula I or a pharmaceutically acceptable salt thereof is administered once daily. In one embodiment, the compound of formula I or a pharmaceutically acceptable salt thereof is administered once daily in a form of a solid oral preparation.

The regimen can be determined comprehensively depending on the activity and toxicity of the medicament, tolerance of the patient, etc. Preferably, the compound of formula I or a pharmaceutically acceptable salt thereof is administered in an intermittent regimen. The intermittent regimen includes treatment periods and rest periods. In the treatment period, the compound of formula I or a pharmaceutically acceptable salt thereof can be administered once or multiple times daily. For example, the compound of formula I or a pharmaceutically acceptable salt thereof is administered daily in the treatment period, and then the treatment is interrupted during the rest period, followed by the treatment period and then the rest period, over and over again. The ratio of the treatment period to the rest period in days is 2:0.5-2:5, preferably 2:0.5-2:3, more preferably 2:0.5-2:2, and most preferably 2:0.5-2:1.

In some embodiments, the treatment is administered for 2 weeks and interrupted for 2 weeks. In some embodiments, the treatment is administered once daily for 14 days, and interrupted for 14 days; and then administered once daily for 14 days, and interrupted for 14 days, etc. Such intermittent regimen in 2-week treatment/2-week rest cycle can be repeated multiple times.

In some embodiments, the treatment is administered for 2 weeks and interrupted for 1 week. In some embodiments, the treatment is administered once daily for 14 days, and interrupted for 7 days; and then administered once daily for 14 days, and interrupted for 7 days, etc. Such intermittent regimen in 2-week treatment/1-week rest cycle can be repeated multiple times.

In some embodiments, the treatment is administered for 5 days and interrupted for 2 days. In some embodiments, the treatment is administered once daily for 5 days, and interrupted for 2 days; and then administered once daily for 5 days, and interrupted for 2 days, etc. Such intermittent regimen in 5-day treatment/2-day rest cycle can be repeated multiple times.

In certain specific embodiments, the treatment is administered once daily at a dose of 12 mg for 2 weeks, and interrupted for 1 week.

In certain specific embodiments, the treatment is administered once daily at a dose of 10 mg for 2 weeks, and interrupted for 1 week.

In certain specific embodiments, the treatment is administered once daily at a dose of 8 mg for 2 weeks, and interrupted for 1 week.

In yet another aspect, the present invention provides a pharmaceutical composition for treating triple-negative breast cancer, comprising the compound of formula I or a pharmaceutically acceptable salt thereof, and at least one pharmaceutically acceptable carrier.

In some embodiments, the triple-negative breast cancer is an advanced or metastatic triple-negative breast cancer.

In some embodiments, the triple-negative breast cancer is refractory to prior treatment.

In some embodiments, the triple-negative breast cancer is refractory to radiotherapy or chemotherapy.

In some embodiments, the triple-negative breast cancer has progressed or relapsed after prior treatment with an anthracycline and/or a taxane. In some embodiments, the triple-negative breast cancer has progressed or relapsed after prior treatment with paclitaxel.

In some embodiments, the triple-negative breast cancer has progressed or relapsed after prior treatment with an antimetabolite. In some embodiments, the triple-negative breast cancer has progressed or relapsed after prior treatment with gemcitabine and/or capecitabine.

In some embodiments, the triple-negative breast cancer has progressed or relapsed after prior treatment with a platinum-based therapy. In some embodiments, the triple-negative breast cancer has progressed or relapsed after prior treatment with cisplatin.

The compound of formula I can be administered in its free base form, or in a form of a salt, a hydrate, or a prodrug that may convert in vivo into the free base form. For example, the pharmaceutically acceptable salt of the compound of formula I can be generated from various organic and inorganic acids according to methods well known in the art, within the scope of the present invention.

In some embodiments, the compound of formula I is administered in a form of hydrochloride. In some embodiments, the compound of formula I is administered in a form of monohydrochloride. In some embodiments, the compound of formula I is administered in a form of dihydrochloride. In some embodiments, the compound of formula I is administered in a crystalline form of hydrochloride. In some embodiments, the compound of formula I is administered in a crystalline form of dihydrochloride. In some embodiments, the compound of formula I is administered in a form of maleate.

The amount of the compound of formula I or a pharmaceutically acceptable salt thereof administered can be determined according to the severity of the disease, the response of the disease, any treatment-related toxicity, and the age and health of a patient. In some embodiments, the daily dose of the compound of formula I or a pharmaceutically acceptable salt thereof is 3 mg to 30 mg. In some embodiments, the daily dose of the compound of formula I or a pharmaceutically acceptable salt thereof is 5 mg to 20 mg. In some embodiments, the daily dose of the compound of formula I or a pharmaceutically acceptable salt thereof is 8 mg to 16 mg. In some embodiments, the daily dose of the compound of formula I or a pharmaceutically acceptable salt thereof is 8 mg to 14 mg. In a specific embodiment, the daily dose of the compound of formula I or a pharmaceutically acceptable salt thereof is 8 mg. In a specific embodiment, the daily dose of the compound of formula I or a pharmaceutically acceptable salt thereof is 10 mg. In a specific embodiment, the daily dose of the compound of formula I or a pharmaceutically acceptable salt thereof is 12 mg.

The pharmaceutical composition may be a preparation suitable for oral, parenteral, intraperitoneal, intravenous, intra-arterial, transdermal, sublingual, intramuscular, rectal, buccal, intranasal, inhalational, vaginal, intraocular, topical, subcutaneous, intralipid, intra-articular, intraperitoneal or intrathecal administrations, preferably a preparation suitable for oral administration, including tablet, capsule, powder, granule, dripping pill, paste and powder, and more preferably a tablet or capsule. The tablet may be a common tablet, dispersible tablet, effervescent tablet, sustained-release tablet, controlled-release tablet or enteric coated tablet. The capsule may be a common capsule, sustained-release capsule, controlled-release capsule or enteric coated capsule. The oral preparation may be prepared by a conventional method using a pharmaceutically acceptable carrier well known in the art. The pharmaceutically acceptable carrier includes fillers, absorbents, wetting agents, binders, disintegrants, lubricants, and the like. The fillers include starch, lactose, mannitol, microcrystalline cellulose, and the like. The absorbents include calcium sulfate, calcium hydrogen phosphate, calcium carbonate, and the like. The wetting agents include water, ethanol, and the like. The binders include hydroxypropyl methylcellulose, polyvidone, microcrystalline cellulose, and the like. The disintegrants include croscarmellose sodium, crospovidone, surfactants, low-substituted hydroxypropyl cellulose, and the like. The lubricants include magnesium stearate, talcum powder, polyethylene glycol, sodium dodecyl sulfate, silica gel micropowder, talcum powder, and the like. The pharmaceutically acceptable carrier further includes coloring agents, sweeteners and the like.

In one embodiment, the pharmaceutical composition is a solid preparation suitable for oral administration. The composition, for example, may be in a form of a tablet or capsule. In one specific embodiment, the pharmaceutical composition is a capsule. In one specific embodiment of the present invention, the pharmaceutically acceptable carrier of the oral solid preparation comprises mannitol, microcrystalline cellulose, hydroxypropylcellulose, and magnesium stearate.

The compound of formula I or the pharmaceutically acceptable salt thereof can be administered once or multiple times daily. In some embodiments, the compound of formula I or the pharmaceutically acceptable salt thereof is administered once daily. In one embodiment, the compound of formula I or the pharmaceutically acceptable salt thereof is administered once daily in a form of a solid oral preparation.

The regimen of the pharmaceutical composition can be determined comprehensively depending on the activity and toxicity of the medicament, tolerance of the patient, etc. Preferably, the compound of formula I or a pharmaceutically acceptable salt thereof or the pharmaceutical composition is administered in an intermittent regimen. The intermittent regimen includes treatment periods and rest periods. In the treatment period, the compound of formula I or a pharmaceutically acceptable salt thereof can be administered once or multiple times daily. For example, the compound of formula I or a pharmaceutically acceptable salt thereof is administered daily in the treatment period, and then the treatment is interrupted during the rest period, followed by the treatment period and then the rest period, over and over again. The ratio of the treatment period to the rest period in days is 2:0.5-2:5, preferably 2:0.5-2:3, more preferably 2:0.5-2:2, and most preferably 2:0.5-2:1.

In some embodiments, the treatment is administered for 2 weeks and interrupted for 2 weeks. In some embodiments, the treatment is administered once daily for 14 days, and interrupted for 14 days; and then administered once daily for 14 days, and interrupted for 14 days, etc. Such intermittent regimen in 2-week treatment/2-week rest cycle can be repeated multiple times.

In some embodiments, the treatment is administered for 2 weeks and interrupted for 1 week. In some embodiments, the treatment is administered once daily for 14 days, and interrupted for 7 days; and then administered once daily for 14 days, and interrupted for 7 days, etc. Such intermittent regimen in 2-week treatment/1-week rest cycle can be repeated multiple times.

In some embodiments, the treatment is administered for 5 days and interrupted for 2 days. In some embodiments, the treatment is administered once daily for 5 days, and interrupted for 2 days; and then administered once daily for 5 days, and interrupted for 2 days, etc. Such intermittent regimen in 5-day treatment/2-day rest cycle can be repeated multiple times.

In certain specific embodiments, the treatment is administered once daily at a dose of 12 mg for 2 weeks, and interrupted for 1 week.

In certain specific embodiments, the treatment is administered once daily at a dose of 10 mg for 2 weeks, and interrupted for 1 week.

In certain specific embodiments, the treatment is administered once daily at a dose of 8 mg for 2 weeks, and interrupted for 1 week.

In yet another aspect, the present invention further provides a kit, comprising (a) at least one unit dose of the pharmaceutical composition comprising the compound of formula I or the pharmaceutically acceptable salt thereof and (b) a package insert for treating triple-negative breast cancer. In some embodiments, a kit is provided, comprising (a) a preparation suitable for oral administration comprising at least one unit dose of the compound of formula I or the pharmaceutically acceptable salt thereof and (b) an package insert for treating triple-negative breast cancer in an intermittent regimen. "Unit dosage" or "unit dose" refers to the pharmaceutical composition contained in a single package for ease of administration, such as a tablet or capsule.

Unless otherwise stated, the dose and ranges provided herein are based on the molecular weight of the free base form for the compound of formula I.

In the method, use, pharmaceutical composition or kit provided herein, the compound of formula I or the pharmaceutically acceptable salt thereof may be administered alone to a patient as the only active ingredient. In the method, use, pharmaceutical composition or kit provided herein, a second active ingredient may be included. The compound of formula I or the pharmaceutically acceptable salt thereof and the second active ingredient are administered to a patient with triple-negative breast cancer concurrently or sequentially. The second active ingredient includes, but is not limited to, a chemotherapeutic drug. The chemotherapeutic drug includes, but is not limited to, anthracyclines, taxanes, platinum-based drugs, capecitabine, cyclophosphamide, and the like.

As used herein, "prior treatment" includes, but is not limited to, one or more of radiotherapy, chemotherapy, and targeted therapy. The targeted therapy includes, but is not limited to, PARP inhibitors (e.g., olaparib, talazoparib) and immunotherapeutics (e.g., PD-L1 inhibitor atezolizumab).

As used herein, the crystalline form of hydrochloride of the compound of formula I includes, but is not limited to, the crystalline form A, the crystalline form B and the crystalline form C disclosed in Chinese Patent No. CN102344438A. The crystalline form A and crystalline form B are substantially free of water and other solvents, and the crystalline form C contains two water molecules. In some embodiments, the crystalline form of dihydrochloride of the compound of formula I is the crystalline form A.

Unless otherwise stated, the following terms used in the specification and claims shall have the following meanings for the purposes of the present invention.

The term "patient" refers to a mammal, and preferably a human.

The term "pharmaceutically acceptable" refers to that when a substance is used for preparing a pharmaceutical composition, the pharmaceutical composition is generally safe, non-toxic, and desirable biologically and otherwise, and inclusion of the substance is acceptable for pharmaceutical use in human.

The "pharmaceutically acceptable salt" includes, but is not limited to, acid addition salts of inorganic acids such as hydrochloric acid, hydrobromic acid, sulfuric acid, nitric acid and phosphoric acid, or acid addition salts of organic acids such as acetic acid, trifluoroacetic acid, propionic acid, hexanoic acid, heptanoic acid, cypionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, p-toluenesulfonic acid, 3-phenylpropionic acid, trimethylacetic acid, t-butylacetic acid, dodecyl sulfuric acid, gluconic acid, glutamic acid, hydroxynaphthoic acid, salicylic acid, and stearic acid.

The term "therapeutically effective amount" refers to an amount of a compound that, when administered to a human for treating a disease, is sufficient to effectively control the disease.

The term "refractory" includes, but is not limited to, disease progression and/or relapse.

The term "therapy" or "treatment" refers to any administration of a therapeutically effective amount of a compound, and is intended to:

(1) suppress a disease in a human experiencing or exhibiting the pathology or symptomatology of the disease (i.e., preventing further pathological and/or symptomatological progression), or (2) relieve the disease in a human experiencing or exhibiting the pathology or symptomatology of the disease (i.e., reversing the pathology and/or symptomatology).

The term "ORR" refers to objective response rate, specifically CR (complete response)+PR (partial response).

The term "CBR" refers to a clinical benefit rate, specifically CR+PR+SD (stable disease).

DETAILED DESCRIPTION

This invention is further illustrated by the following examples, which should not be construed as limiting.

Example 1 1-[[[4-(4-fluoro-2-methyl-1H-indol-5-yl)oxy-6-methoxyquinolin-7-yl]oxy]methyl]cyclopropylamine dihydrochloride

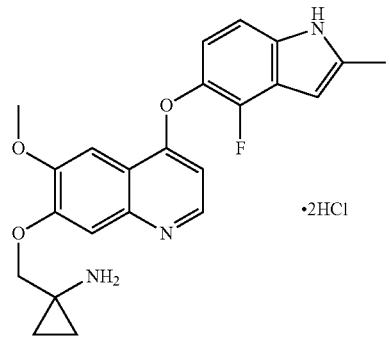 [SMILES: COc1cc2c(Oc3ccc4[nH]c(C)cc4c3F)ccnc2cc1OCC1(N)CC1]

1-[[[4-(4-fluoro-2-methyl-1H-indol-5-yl)oxy-6-methoxyquinolin-7-yl]oxy]methyl]cyclopropylamine was prepared as per the Example 24 of International Publication No. WO2008112407, and then the titled compound was prepared as per the preparation method of "Examples of salt formation" in the specification of WO2008112407.

Or, the titled compound may be prepared as per the method disclosed in Chinese Publication No. CN102344438A.

Example 2 Preparation of Capsules Containing 1-[[[4-(4-fluoro-2-methyl-1H-indol-5-yl)oxy-6-methoxyquinolin-7-yl]oxy]methyl]cyclopropylamine dihydrochloride (Dihydrochloride of the Compound of Formula I)

| active ingredient/excipients | amount (1000 capsules) |
| --- | --- |
| Dihydrochloride of the compound of formula I | 14.16 g (equivalent to 12 g of the compound of formula I) |
| Mannitol | 89 g |
| Microcrystalline cellulose | 138.4 g |
| Hydroxypropyl cellulose | 5.9 g |
| Magnesium stearate | 0.99 g |

The dihydrochloride of the compound of formula I was ground, sieved with an 80-mesh sieve, and well mixed with mannitol and hydroxypropyl cellulose. A predetermined amount of microcrystalline cellulose was added, and the resulting mixture was well mixed and sieved with a 0.8-mm sieve. Finally, a predetermined amount of magnesium stearate was added and the resulting mixture was well mixed to fill capsules.

Capsules with different amount of the dihydrochloride of the compound of formula I can be prepared as per the same proportions and ingredients as described above.

Example 3 Clinical Trial

Clinical trials of dihydrochloride capsules of the compound of formula I were conducted in patients with advanced or metastatic triple-negative breast cancer (ER-negative, PR-negative, HER2-negative) aged ≥18 years, having measurable lesions (according to RECIST 1.1), and previously had received or not received chemotherapy. The dihydrochloride capsules of the compound of formula I were administered alone, or in combination with chemotherapy, in a regimen of two-week treatment at 12 mg once daily, followed by one-week rest, i.e., in a 3-week treatment cycle. The outcome measurements included: efficacy, e.g., progression-free survival (PFS), objective response rate (ORR), duration of response (DOR), stable disease (SD) rate, clinical benefit rate (CBR), overall survival (OS), etc.; safety, e.g., incidence and severity of adverse events; and quality of life.

The clinical trial demonstrated that the dihydrochloride of the compound of formula I was effective for the treatment of triple-negative breast cancer, and leading to a variety of clinical benefits for patients.

Example 4

A 32-year-old female patient who had undergone right breast tumor resection. The postoperative pathology showed sarcomatoid carcinoma in the right breast. The patient was treated with six cycles of chemotherapy, with a best overall response of PR. The lower part of the lesion involved the chest wall. After chemotherapy, disease relapsed (multiple nodules and bumps on the anterior chest wall) in a follow-up examination. The disease progressed after 2 cycles of chemotherapy, then radiotherapy was given. After the right breast tumor resection, the pathological consultation judged that the breast tumor relapsed, and the immunohistochemical result indicated ER(−), PR(−) and HER2(−).

The patient received the dihydrochloride capsules of the compound of formula I in a regimen of two-week treatment at 12 mg once daily, followed by one-week rest, i.e., in a 3-week treatment cycle. After four treatment cycles, radiography in neck, chest and brain suggested stable disease. After ten treatment cycles, the assessment suggested stable disease and the therapy was well tolerated.

Example 5

A 54-year-old female diagnosed with breast cancer by B-scan ultrasonography and breast tumor biopsy. The patient had undergone a modified radical mastectomy in the left breast, and the postoperative pathology indicated stage II invasive ductal carcinoma, without invading the nipple. The immunohistochemical result showed ER(−), PR(−), and HER-2(−). The patient received 4 courses of adjuvant chemotherapy and 1 course of radiotherapy. Recurrence in the chest wall was observed at the time of one-year follow-up examination after the surgery. Then NP chemotherapy (vinorelbine+cisplatin) was given for 2 cycles prior to the disease progression. The patient was again subjected to chest wall tumor resection and axillary lymphangiectomy. The postoperative pathology showed chest wall and axillary carcinoma, and diagnosed as recurrent and metastatic breast cancer. The immunohistochemical result showed ER(−), PR(−), and HER-2(−). After the surgery, treatment of gemcitabine and capecitabine chemotherapy was given for four weeks, however, metastases to lung, liver and bone was observed in a follow-up examination. The patient was then treated with nab-paclitaxel before progressive disease was noted. Image of radiography showed a lesion in liver (2.3 cm, long diameter) and a right adrenal metastatic tumor (5.6 cm, long diameter). The patient received the dihydrochloride capsules of the compound of formula I in a regimen of two-week treatment at 12 mg once daily, followed by one-week rest, i.e., in a 3-week treatment cycle. After two treatment cycles, the follow-up examination indicated significant reduction in metastatic lesions, lesions in the liver reduced to 1.8 cm (long diameter), and the right adrenal gland metastatic tumor reduced to 4.6 cm (long diameter). The treatment was given until disease progression.

What is claimed is:

1. A method of treating triple-negative breast cancer in a patient, the method comprising administering to the patient in need thereof a therapeutically effective amount of a compound of formula I or a pharmaceutically acceptable salt thereof,

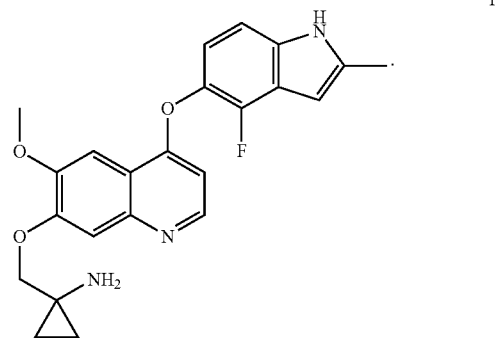

2. The method of claim 1, wherein the triple-negative breast cancer is advanced or metastatic triple-negative breast cancer.

3. The method of claim 1, wherein the triple-negative breast cancer is refractory to prior treatment.

4. The method of claim 1, wherein the triple-negative breast cancer is refractory to radiotherapy and/or chemotherapy.

5. The method of claim 3, wherein the prior treatment comprises at least one treatment selected from the group consisting of radiotherapy, chemotherapy, and targeted therapy.

6. The method of claim 5, wherein the prior treatment is at least one of an anthracycline, a taxane, ara antimetabolite, and a platinum-based therapy.

7. The method of claim 1, wherein the pharmaceutically acceptable salt is a salt formed by the compound of formula I and an acid selected from the group consisting of hydrochloric acid, hydrobromic acid, sulfuric acid, nitric acid, phosphoric acid, acetic acid, trifluoroacetic acid, propionic acid, hexanoic acid, heptanoic acid, cypionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, p-toluenesultbnic acid, 3 phenylpropionic acid, trimethylacetic acid, t-butylacetic acid, dodecyl sulfuric acid, gluconic acid, glutamic acid, hydroxynaphthoic acid, salicylic acid, and stearic acid.

8. The method of claim 1, wherein the pharmaceutically acceptable salt is a hydrochloride or a maleate salt.

9. The method of claim 1, wherein the compound of formula I or the pharmaceutically acceptable salt thereof is administered via oral, parenteral, intraperitoneal, intravenous, intra-arterial, transdermal, sublingual, intramuscular, rectal, buccal, intranasal, inhalational, vaginal, intraocular, topical, subcutaneous, intralipid, intra-articular, intraperitoneal or intrathecal route.

10. The method of claim 1, wherein the compound of formula I or the pharmaceutically acceptable salt thereof is administered orally.

11. The method of claim 1, wherein the daily dose of the compound of Formula I or the pharmaceutically acceptable salt administered is selected from the group consisting of 3 mg to 30 mg, 5 mg to 20 mg, 8 mg to 16 mg, 8 mg to 14 mg, 8 mg, 10 mg. and 12 mg.

12. The method of claim 1, wherein the daily dose of the compound of Formula I or the pharmaceutically acceptable salt administered is 8 mg, 10 mg, or 12 mg.

13. The method of claim 1, wherein the compound of Formula I or the pharmaceutically acceptable salt thereof is administered by an intermittent regimen including treatment periods and rest periods, and the ratio of the treatment period to the rest period in days is 2:0.5~2:5, 2:0.5~2:3, 2:0.5~2:2, or 2:0.5~2:1.

14. The method of claim 1, wherein the compound of Formula I or the pharmaceutically acceptable salt thereof is administered by an intermittent regimen selected from the group consisting of: 2-week treatment period/2-week rest period, 2-week treatment period/1-week rest period, and 5-day treatment period/2-day rest period.

15. The method of claim 1, wherein the compound of Formula I or the pharmaceutically acceptable salt thereof is administered by an intermittent regimen, wherein the treatment is administered for two weeks, and rested for 1 week.

16. The method of claim 1, wherein a second active ingredient is administered concurrently or sequentially with the compound of Formula I or the pharmaceutically acceptable salt thereof.

17. The method of claim 16, wherein the second active ingredient is a chemotherapeutic drug.

18. The method of claim 17, wherein the chemotherapeutic drug is selected from the group consisting of an anthracycline, a taxane, a platinum-based drug, capecitabine, and cyclophosphamide.

19. The method of claim 1, wherein the patient is a human.

20. The method of claim 3, wherein the triple-negative breast cancer has progressed or relapsed after the prior treatment selected from the group consisting of Baa anthracycline, a taxane, an antimetabolite, and a platinum-based therapy.

* * * * *